(12) United States Patent
Malaney et al.

(10) Patent No.: US 8,937,475 B2
(45) Date of Patent: Jan. 20, 2015

(54) SYSTEMS AND METHODS FOR NOISE CONTROL IN A MEDICAL IMAGING SYSTEM

(75) Inventors: James Malaney, Pewaukee, WI (US); Jennifer Black, Pewaukee, WI (US)

(73) Assignee: General Electric Company, Schenectady, NY (US)

(*) Notice: Subject to any disclaimer, the term of this patent is extended or adjusted under 35 U.S.C. 154(b) by 471 days.

(21) Appl. No.: 13/470,442

(22) Filed: May 14, 2012

(65) Prior Publication Data

US 2013/0300417 A1    Nov. 14, 2013

(51) Int. Cl.
*G01V 3/00*    (2006.01)

(52) U.S. Cl.
USPC .......................................... 324/322; 324/318

(58) Field of Classification Search
USPC .......... 324/322, 318, 314, 300; 323/211, 283, 323/351
See application file for complete search history.

(56) References Cited

U.S. PATENT DOCUMENTS

| | | | | |
|---|---|---|---|---|
| 5,134,355 A | * | 7/1992 | Hastings | 323/211 |
| 6,577,510 B1 | * | 6/2003 | Yasumura | 363/21.02 |
| 7,504,815 B2 | * | 3/2009 | Moyse et al. | 323/351 |
| 8,258,768 B2 | * | 9/2012 | McPhalen et al. | 323/283 |
| 8,829,905 B2 | * | 9/2014 | Davila et al. | 324/322 |
| 2011/0124301 A1 | | 5/2011 | Prasidh et al. | |
| 2011/0291657 A1 | | 12/2011 | Davila et al. | |

* cited by examiner

*Primary Examiner* — Louis Arana
(74) *Attorney, Agent, or Firm* — Dean D. Small; The Small Patent Law Group

(57) ABSTRACT

A noise abatement system includes a processor configured to measure noise in an imaging system and generate a switch mode power supply (SMPS) input signal based on the measured noise and an adjustable switched mode power supply configured to receive the SMPS input signal and adjust a switching frequency of the switched mode power supply, based on the SMPS signal, to operate at a frequency that generates harmonics that are outside of an imaging bandwidth of the imaging system. A system and calibration method are also described herein.

20 Claims, 4 Drawing Sheets

SYSTEMS AND METHODS FOR NOISE CONTROL IN A MEDICAL IMAGING SYSTEM

BACKGROUND OF THE INVENTION

The subject matter disclosed herein relates generally to imaging systems, and more particularly to a noise control system, such as for a Magnetic Resonance Imaging (MRI) system.

MRI is a medical imaging modality that generates images of the inside of a human body without using x-rays or other ionizing radiation. The MRI system utilizes radio frequency (RF) coils to amplify radio frequency signals emitted by atoms in a human or animal body after being excited by an RF pulse while being subjected to a constant magnetic field.

In operation, the MRI imaging system is sensitive to RF noise that overlaps with the operating frequency of the MRI system. Accordingly, the MRI receive circuitry should be free from spurious noise that coincides with the operating frequency of the MRI system. To reduce the spurious noise, peripheral devices utilized within the MRI system, or located near the MRI system, are typically evaluated to determine if the peripheral devices generate harmonic signals that may interfere with the MRI system operating and thus may cause spurious noise.

For example, one known potential source of spurious noise is a power supply that provides power to the MRI system and/or the peripheral devices. At least one known power supply utilized with the MRI system is a linear power supply. In operation, the linear power supply generates power having a frequency that is preselected to not generate spurious noise. However, conventional linear power supplies operate within a predetermined frequency band or range. Accordingly, in operation, the linear power supply may still generate signals having harmonics that result in spurious noise. Moreover, conventional linear power supplies and associated regulators are relatively large, heavy, inefficient and expensive.

BRIEF DESCRIPTION OF THE INVENTION

In one embodiment, a noise abatement system is described. The noise abatement system includes a processor that is configured to measure noise in an imaging system. The processor generates a switch mode power supply (SMPS) input signal based on the measured noise. An adjustable switched mode power supply is configured to receive the SMPS input signal and adjusts a switching frequency of the switched mode power supply, based on the SMPS signal, to operate at a frequency that generates harmonics that are outside of an imaging bandwidth of the imaging system.

In another embodiment, a magnetic resonance imaging (MRI) system is described. The MRI system includes an RF coil and a noise abatement system coupled to the RF coil. The noise abatement system includes a processor configured to receive RF information from the RF coil, measure noise in the MRI system using the RF information, and generate a switch mode power supply (SMPS) input signal based on the measured noise. An adjustable switched mode power supply is configured to receive the SMPS input signal and adjusts a switching frequency of the switched mode power supply, based on the SMPS signal to operate at a frequency that generates harmonics that are outside of an imaging bandwidth of the MRI system.

In a further embodiment, a method for calibrating a MRI system is provided. The method includes measuring noise in the MRI imaging system, generating a signal based on the measured noise, and adjusting a switching frequency of a switched mode power supply (SMPS) based on the signal to operate at the system at a frequency that generates harmonics that are outside of an imaging bandwidth of the MRI imaging system.

DETAILED DESCRIPTION OF THE INVENTION

Figure 1:
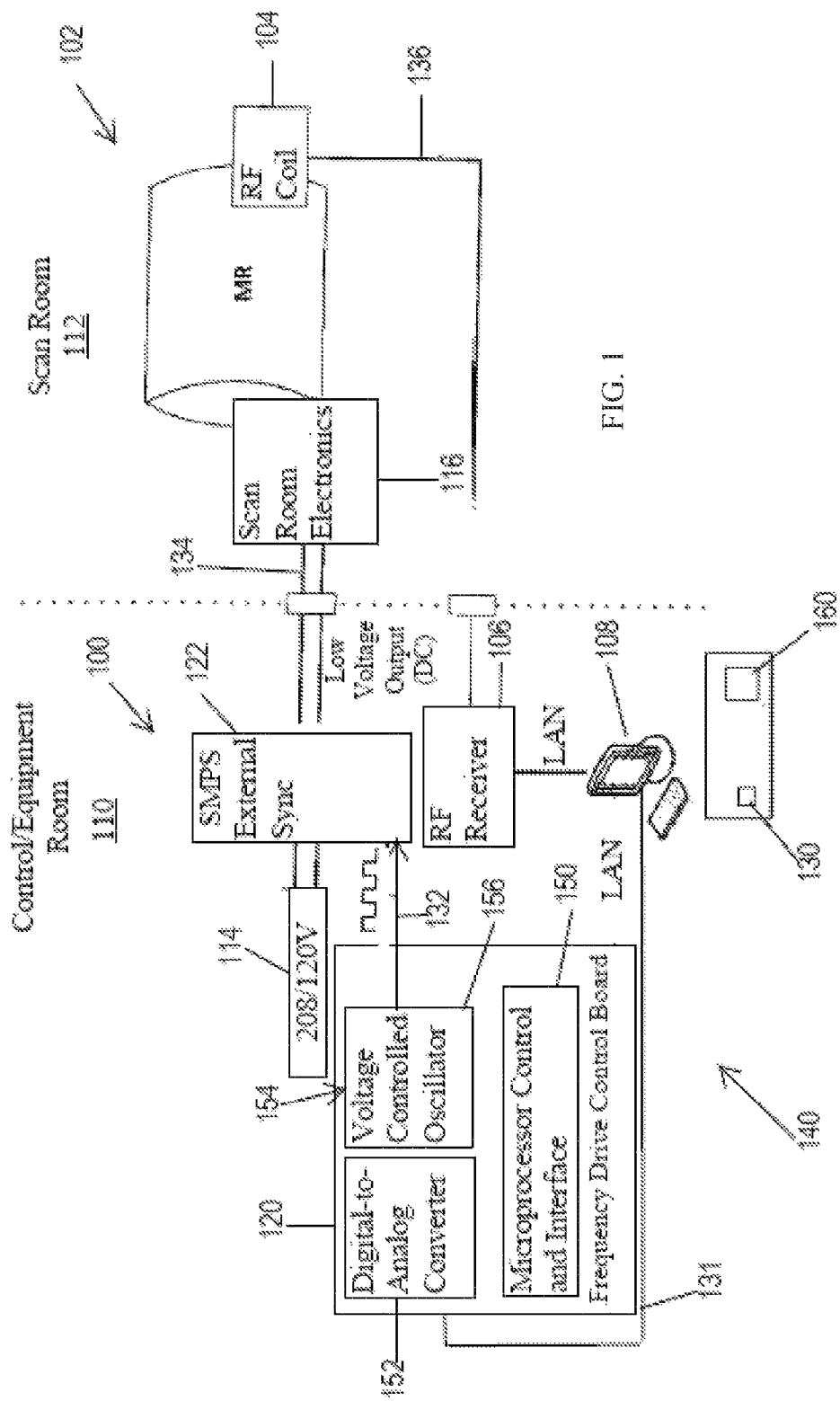
FIG. 1 is a simplified block diagram of a noise control system formed in accordance with various embodiments.

Embodiments of the invention will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a noise abatement system (NACS) that is utilized to reduce and/or eliminate spurious noise that may interfere with the operation of a Magnetic Resonance Imaging (MRI) system. The NACS includes an adjustable switched mode power supply (SMPS) that is configured to supply power to the MRI system. In operation, the SMPS receives an input from an external source and, based on the received input, outputs a power signal having switching frequency harmonics that are outside an imaging bandwidth of the MRI system.

FIG. 1 is a simplified block diagram illustrating a NACS 100 formed in accordance with various embodiments. In operation, the NACS 100 is configured to provide a power supply to a system. In the illustrated embodiment, the system is a MRI system 102. However, it should be realized that the NACS 100 may be configured to supply power to any system. For example, in various other embodiments, the system 102 may be a Positron Emission Tomography (PET) system, a Single Photon Emission Computed Tomography (SPECT) system, a Computed Tomography (CT) imaging system, an Ultrasound imaging system, and/or an X-ray system, among others. The MRI system 102 includes at least an RF coil 104 and an RF receiver 106. In operation, the output from the RF coil 104, which may be a single RF coil or an array of RF coils, is transmitted to the RF receiver 106. An output from the RF receiver 106 may then be transmitted to a processor or workstation 108 for additional processing as described in more detail below.

In the illustrated embodiment, the NACS 100 is located in a control/equipment room 110 and the MRI system 102 is located in a separate scan room 112. In other embodiments, the NACS 100 may be located in the scan room 112 with the MRI system 102. The MRI system 102 is configured to receive power from a power supply 114 which is controlled by the NACS 100. In various embodiments, the input to the power supply 114 may be any voltage or frequency that may be utilized to operate the MRI system 102, including the scan room electronics 116. It should be realized that the actual power, including the operating frequency of the power supplied to the MRI system 102 may be controlled or regulated using the NACS 100 as is discussed in more detail below.

In various embodiments, the NACS 100 includes a frequency drive control device 120 and a switched mode power supply (SMPS) 122 that is coupled to the frequency drive control device 120. The frequency drive control device 120 may be implemented as a printed circuit board (PCB). More specifically, the various devices or components forming the frequency drive control device 120 may, in various embodiments, be mounted onto a single PCB.

In operation, the workstation 108 sends a command 130, which may also be referred to as a NACS input signal, to the NACS 100 over a communication link 131 instructing the NACS 100 to either increase or decrease its frequency. Based on the command 130, the frequency drive control device 120 is configured to output a signal, referred to herein as the SMPS input signal 132, to the SMPS 122. In operation, the SMPS input signal 132 controls the operation of the SMPS 122 such that the SMPS 122 outputs a power signal 134 to the MRI system 102. More specifically, the RF information 136 from the RF coil 104 is transmitted to the workstation 108 via the RF receiver 106. The workstation 108 performs various processing techniques based on the RF information 136 to generate the command 130 which is utilized by the NACS 100 to generate the SMPS input signal 132.

In operation, the RF information 136 is transmitted from the MRI system 102 to the NACS 100, via the workstation 108, using a communication network 140. In various embodiments, the communication network 140 may be implemented as a local area network (LAN). For example, a portion of the communication network 140 may be implemented as a Wi-Fi network (IEEE 802.11) to enable the workstation 108 to communicate wirelessly with the NACS 100 or to enable the RF coil 104 to wirelessly transmit information to the workstation 108.

In other embodiments, a portion of the communication network 140 may be implemented using a wired connection, such as for example, by a wired IEEE 802.3 (Ethernet) connection and/or a universal service bus (USB) connection. For example, the RF receiver 106 may be connected to the workstation 108 using a wired connection and the workstation 108 may be wirelessly coupled to the NACS 100 using a Wi-Fi system. In other embodiments, the RF receiver 106 may communicate with the workstation 108 via Ethernet while the workstation 108 communicates with the NACS 100 via USB connections. Moreover, the workstation 108 may function as a router to enable the RF receiver 106 to communicate with the workstation 108 and the NACS 100 via the Internet. While various embodiments are described with respect to a healthcare setting, the NACS 100 may be used in non-healthcare settings.

In various embodiments, the NACS 100 includes a processor 150, a digital-to-analog (D/A) converter 152, and a variable frequency generator 154. In the illustrated embodiment, the variable frequency generator 154 is a voltage controlled oscillator 156. However, it should be realized that other implementations may be utilized. Such implementations include for example, a field-programmable gate array (FPGA) having a phase-locked loop, among others.

In operation, the processor 150 is configured to receive the command 130 and perform various processing techniques on the command 130 to enhance the quality of the command 130 for subsequent processing. The various processing techniques may include for example, filtering the command 130, smoothing the command 130, etc.

After being processed by the processor 150, the output is transmitted to the D/A converter 152. In operation, the D/A converter 152 receives digital information from the processor 150 that is generated based on the command 130, and converts the digital information to an analog signal that controls the voltage controlled oscillator 156.

In general, the variable frequency generator 154 is configured to generate a digital trigger pulse at a repetition frequency that is based upon the NACS input information from the processor 150 or workstation 108. In operation, the frequency is based upon the input received from the D/A converter 152 and more specifically, on the NACS input information from the processor 150 or workstation 108. As described above, in the illustrated embodiment, the variable frequency generator 154 is implemented as a voltage controlled oscillator 156. The voltage controlled oscillator 156 is configured to utilize the NACS input information from the workstation 108 to generate the SMPS input signal 132. More specifically, the voltage controlled oscillator 156 control the repetition frequency of the SMPS input signal 132 based upon the NACS input information from the workstation 108. Thus, information from the workstation 108 to the NACS 100, allows for control of the voltage controlled oscillator 156 to change the frequency of the SMPS input signals 132.

The SMPS 122 is configured to provide power to the MRI system 102. More specifically, the SMPS is configured to control the frequency at which the SMPS 122 operates at to regulate the voltage. In various embodiments, the SMPS 122 may include for example, several stages to control the voltage of power supplied to the MRI system 102 and/or the scan room electronics 116. For example, the SMPS 122 may include an input filtering stage to reduce and/or eliminate electrical interference in the power supplied to the SMPS 122 from the power supply 114. The SMPS 122 may include a primary rectifier that converts the AC current from the power supply 114 into a pulsed, non-continuous DC waveform. The SMPS 122 may also include a plurality of primary capacitors for smoothing the non-continuous DC waveform into a substantially smoothed constant DC waveform. The SMPS 122 may also include a plurality of switching transistors, or switchers, for transforming the smoothed constant DC waveform back to a non-continuous or pulsed DC waveform. It should be realized that the frequency of the pulsed DC waveform, in the exemplary embodiment, is controlled based on the command 130. The SMPS 122 may also include at least one transformer to modify the voltage level of the signal received from the power supply 114 to a voltage level usable by the MRI system 102. The SMPS 122 may also include at least one rectifier, such as a bridge rectifier, to enable the pulsed DC waveform to flow in only a single direction. The SMPS 122 may additionally include an output filtering stage configured to smooth out the ripples in the DC voltage output signal which may be generated by the switching transistors. Accordingly, the power signal 134 is a DC voltage regulated by the SMPS 122 operating at a frequency based upon the command 130. In various embodiments, the workstation 108 includes a noise analysis module 160 that is configured to generate the command 130 as is described in more detail below. It should be realized that the SMPS 122 may be implemented with circuitry or components that are different than the circuitry and components described above.

Figure 2:
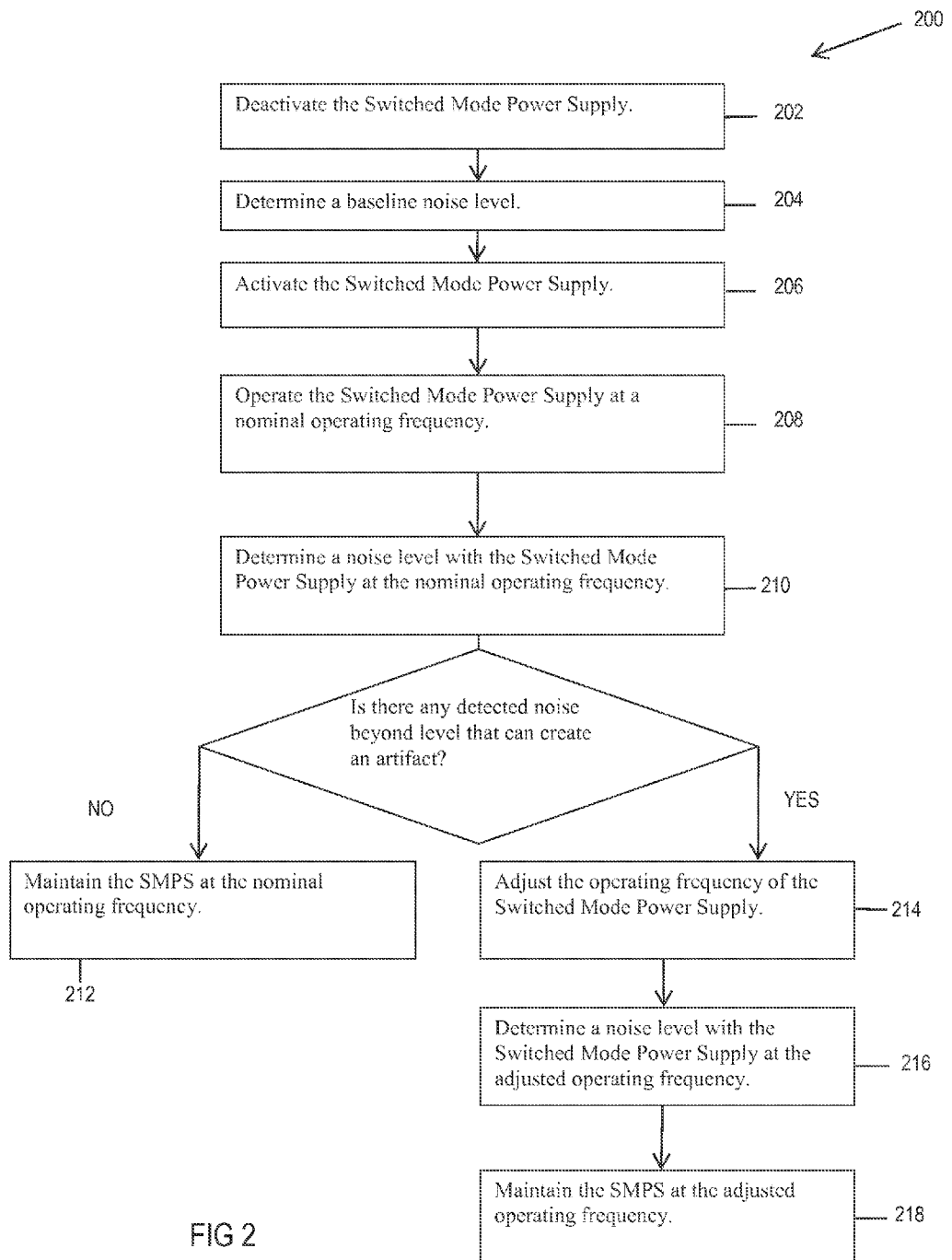
FIG. 2 is a flowchart of a method for calibrating an imaging system in accordance with various embodiments.
Figure 3:
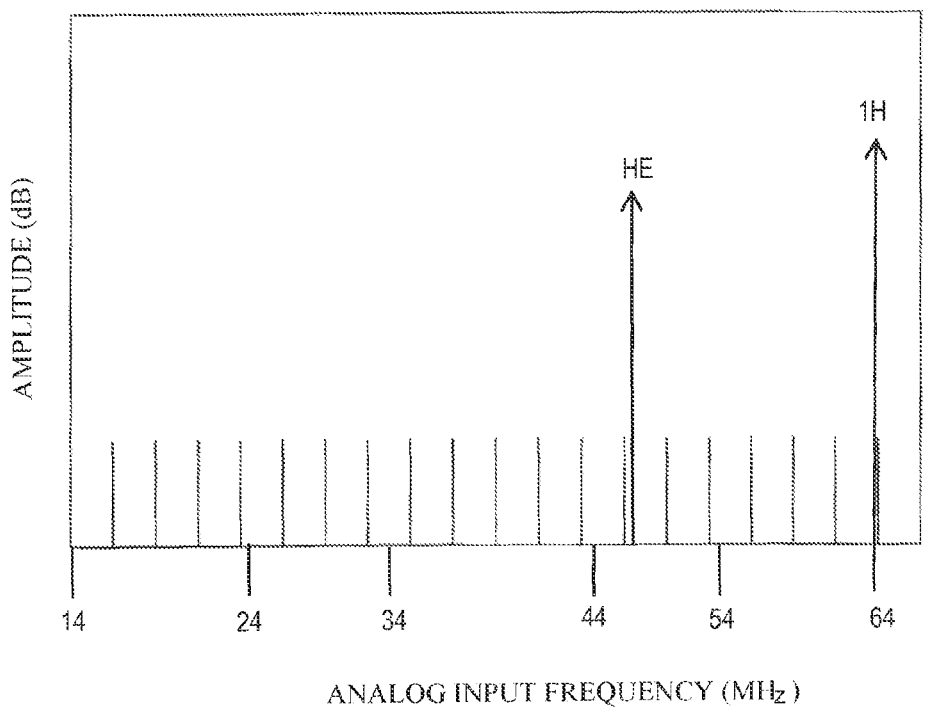
FIG. 3 is a graphical illustration of various resonance frequencies which may be utilized by the system shown in FIG. 1 in accordance with various embodiments.

FIG. 2 is a flowchart of a method 200 of calibrating a system, such as the MRI system 102 shown in FIG. 1. In operation, spurious noise may occur when a device utilized with the MRI system 102, such as the power supply 114 is operating at such a frequency, that harmonics are generated that may interfere with the operation of the MRI system 102. More specifically, the RF coil 104 may be used to create pulses of RF energy at or near the resonance frequency of various nuclei desired to be detected. For example, FIG. 3 is a graphical illustration of various resonance frequencies which may be utilized by the MRI system 102. In the illustrated embodiment, the RF coil 104 may be tuned to the resonance frequency of hydrogen nuclei, also referred to herein as the Larmor frequency, which in the exemplary embodiment, is 64 MHz for a 1.5 Tesla (T) MRI system. In various other embodiments, the RF coil 104 may be tuned to the resonance frequency of helium, which in the exemplary embodiment, is 48 MHz for a 1.5 T MRI system. It should be realized that the RF coil 104 may be tuned to any desired frequency and the frequencies illustrated in FIG. 3 are exemplary only.

Referring again to FIG. 2, at 202, the SMPS 122 is deactivated. At 204, a baseline noise level is determined with the SMPS deactivated In various embodiments, the baseline noise level may be determined utilizing, for example, the noise analysis module 160 shown in FIG. 1 As used herein, the term "module" or "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The baseline noise level is determined to identify noise that may be affecting the image quality of an image generated using the MRI system 102 while the SMPS 122 is deactivated. The noise analysis module 160 is then utilized to identify any component generating harmonic frequencies that coincide with the Larmor frequency of the nuclei being detected by the MRI system 102 and which may then result in spurious noise in the generated image. Such spurious noise may be generated, for example, by leakage within the scan room 112 or various other components associated with the MRI system 102. Accordingly, determining a baseline noise level at 202 includes identifying any component or device, whether inside the scan room 112 or not, that is generating a signal having a frequency that substantially coincides with the Larmor frequency of the nuclei being detected by the RF coil 104 while the SMPS 122 is deactivated.

In various embodiments, the baseline noise level may be determined by separately operating various components in the MR acquisition chain. More specifically, a single component may be operated while the RF coil 104 is concurrently providing the RF information 136 to the workstation 108, e.g. the noise analysis module 160. The noise analysis module 160 then analyzes the RF information 136 to determine if any of the signals in the RF information 136 are generating harmonics that coincides with the Larmor frequency of the nuclei being detected by the RF coil 104 while the SMPS 122 is deactivated.

In various embodiments, the noise analysis module 160 may perform a coherent noise test on the RF information 136 to identify whether the component currently operating is generating a signal that has harmonics that may be synchronous or coincide with the operational frequency of the MRI system 102. A coherent noise test, as used herein, is a test performed on the RF information 136 to identify potential sources of interference, e.g. signals that are coherent with the MRI operating frequency that may corrupt the signal and affect a subsequently generated image. It should be realized that a plurality of different diagnostic tests may be utilized by the MRI system 102 to identify coherent noise, and the coherent noise test described herein is an embodiment of one such test. In various embodiments, the results of the coherent noise test may be a list of coherent and/or synchronous frequencies that are above a predetermined threshold and therefore may cause artifacts in the generated image. The list may be displayed to a user of the workstation 108 to enable the user to activate and/or deactivate the various components to confirm the source of the frequencies on the list. Optionally, a user may observe an image at the workstation 108 to determine if there are artifacts caused by coherent noise.

The coherent noise test may be performed on the MRI system 102, and the various components, in an iterative manner while the user activates and/or deactivates various components while substantially concurrently reviewing the list of frequencies shown on the list. While the embodiment described above may be implemented manually by the user, it should be realized that in various embodiments, the coherent noise test may be automatically performed by the MRI imaging system 102. After any potential sources of coherent noise have been identified and eliminated, the method proceeds to step 206.

At step 206, the SMPS 122 is activated or powered on. At 208, the command 130 directs the SMPS 122 to operate at a nominal, or initial, operating frequency. More specifically, the NACS input signal 132 is transmitted to the frequency drive control device 120 to generate the SMPS input signal 132 and operate the SMPS at an initial nor nominal operating frequency. The SMPS input signal 132 is then transmitted to the SMPS 122 which controls the frequency of the power signal 134, which is input to the MRI system 102 based upon the command 130 as described above.

At 210, a noise level of the SMPS 122 is determined while the SMPS 122 is operating at the nominal frequency. As described above, the SMPS 122 noise level may be determined utilizing, for example, the noise analysis module 160 shown in FIG. 1. The SMPS 122 noise level is determined to identify noise that may be affecting the image quality of an image generated that is caused by the SMPS 122. To determine the SMPS 122 noise level, the noise analysis module 160 analyzes the RF information 136 acquired while the SMPS 122 is activated to determine if any of the signals in the RF information 136, received from the RF coil 104, are generating harmonics that coincide with the Larmor frequency of the nuclei being detected by the RF coil 104 while the SMPS 122 is activated.

As described above, the noise analysis module 160 may perform a coherent noise test on the RF information 136 to identify whether the SMPS 122 is generating a signal that has harmonics that may be synchronous or coincide with the operational frequency of the MRI system 102. However, it should again be realized that a plurality of different diagnostic tests may be utilized by the MRI system 102 to identify coherent noise, and the coherent noise test described herein is an embodiment of one such test. In various embodiments, the results of the coherent noise test performed on the SMPS 122 may be a list of coherent and/or synchronous frequencies that are above a predetermined threshold and therefore may cause artifacts in the generated image. In other embodiments, a user may identify coherent noise by identifying whether any artifacts are present in the generated image.

In one embodiment, if the results of the coherent noise test are negative, e.g. the coherent noise test shows that the SMPS 122 is not generating coherent noise, then at 212, the command 130 directs the SMPS 122 to operate at the initial or nominal frequency set prior to the coherent noise test being performed at 210. Optionally, if the results of the coherent noise test are positive, e.g. the coherent noise test shows that the SMPS 122 is generating coherent noise at the desired operational frequency, at 214, the command is utilized to adjust the operating frequency of the SMPS 122.

In the exemplary embodiment, to modify the switching frequency of the SMPS 122, the voltage level of the command 130 is modified. The voltage level of the command 130 may be varied higher or lower to increase or decrease the switching frequency of the SMPS 122 until the image artifacts have been substantially reduced and/or eliminated. For example, as described above, the SMPS 122 is initially set to the nominal operating frequency, which in this embodiment, results in coherent noise.

Accordingly, to reduce and/or eliminate the coherent noise caused by the SMPS 122, at 214, the noise analysis module 160 may be configured to automatically iteratively perform coherent noise tests on the RF information 136 to identify signals of the SMPS 122 that have harmonics that may be synchronous or coincide with the operational frequency of the MRI system 102. In various embodiments, at 214 the operating frequency of the SMPS 122 is adjusted by adjusting the voltage level of the command 130. More specifically, the command 130 may be incremented or decremented, to increment or decrement the operating frequency of the SMPS 122, while substantially concurrently identifying whether artifacts have increased, decreased and/or eliminated.

For example, assume that the desired operational frequency of the MRI system 102 is 48 MHz, e.g. the Larmor frequency of the hydrogen nuclei. Moreover, assume that the SMPS 122 is operating at a nominal switching frequency of 1.6 MHz. It should then be realized that every $30^{th}$ harmonic generated by the SMPS 122 coincides with the Larmor frequency of the hydrogen nuclei, e.g. 48 MHz as shown in FIG. 3. Thus, in the exemplary embodiment, the switching frequency of the SMPS 122 is incremented or decremented, using the command 130, such that the switching frequency is not 1.6 MHz. In various embodiments, the operating frequency of the SMPS 122 may is adjusted in predetermined steps. For example, the switching frequency of the SMPS 122 may be increased from 1.6 MHz to 1.7 MHz, e.g. incremented in steps of 0.1 MHz. It should be realized that incremental steps of 0.1 MHz are exemplary only and that the switching frequency of the SMPS may be incremented or decremented in steps of any desired frequency.

At 216, after the switching frequency of the SMPS 122 has been adjusted, the noise analysis module 160 is again configured to automatically perform a coherent noise test on the RF information 136, at the adjusted value of 1.7 MHz, for example, to identify whether the SMPS 122 is generating a signal that has harmonics that may be synchronous or coincide with the operational frequency of the MRI system 102. In one embodiment, if the results of the coherent noise test are negative, e.g. the coherent noise test shows that the SMPS 122 is not generating coherent noise at the adjusted frequency, then at 218, the command 130 maintains the adjusted frequency set at 214. If the results of the coherent noise test are positive, e.g. the coherent noise test shows that the SMPS 122 is generating coherent noise at the adjusted operational frequency, the method returns to 214, and the operating frequency of the SMPS 122 is adjusted and tested at 216. In various other embodiments, the noise analysis module 160 may be configured to increase the switching frequency of the SMPS 122 until coherent noise is generated. The noise analysis module 160 may then reduce the switching frequency of the SMPS 122 until the coherent noise is substantially reduced below a predetermined threshold and/or eliminated. The noise analysis module 160 may be further configured to continue reducing the switching frequency of the SMPS 122 until the coherent noise re-appears. In this embodiment, the noise analysis module 160 automatically identifies a first threshold where coherent noise is produced, an intermediate threshold where coherent noise is reduced, and a third threshold where coherent noise is again increased. The noise analysis module 160 may then identify a center or null point between the first and third threshold and set the switching frequency of the SMPS at the identified null point.

A technical effect of at least one embodiment described herein is a system that automatically or manually identifies spurious noise in an imaging system that may be caused by a SMPS. The system automatically generates a signal based on the noise and then transmits the signal to the SMPS to modify the switching frequency of the SMPS until the spurious noise is reduced and/or eliminated. Using the adjustable SMPS enables more common power distribution devices and architectures that implement higher voltage distribution cabling and local switching converters to be utilized by the MRI system. The adjustable SMPS may also reduce power losses associated with distribution of low voltages at high current over resistive cabling and may operate at greater than 90% efficiency to reduce power consumption and minimize heat loss.

Figure 4:
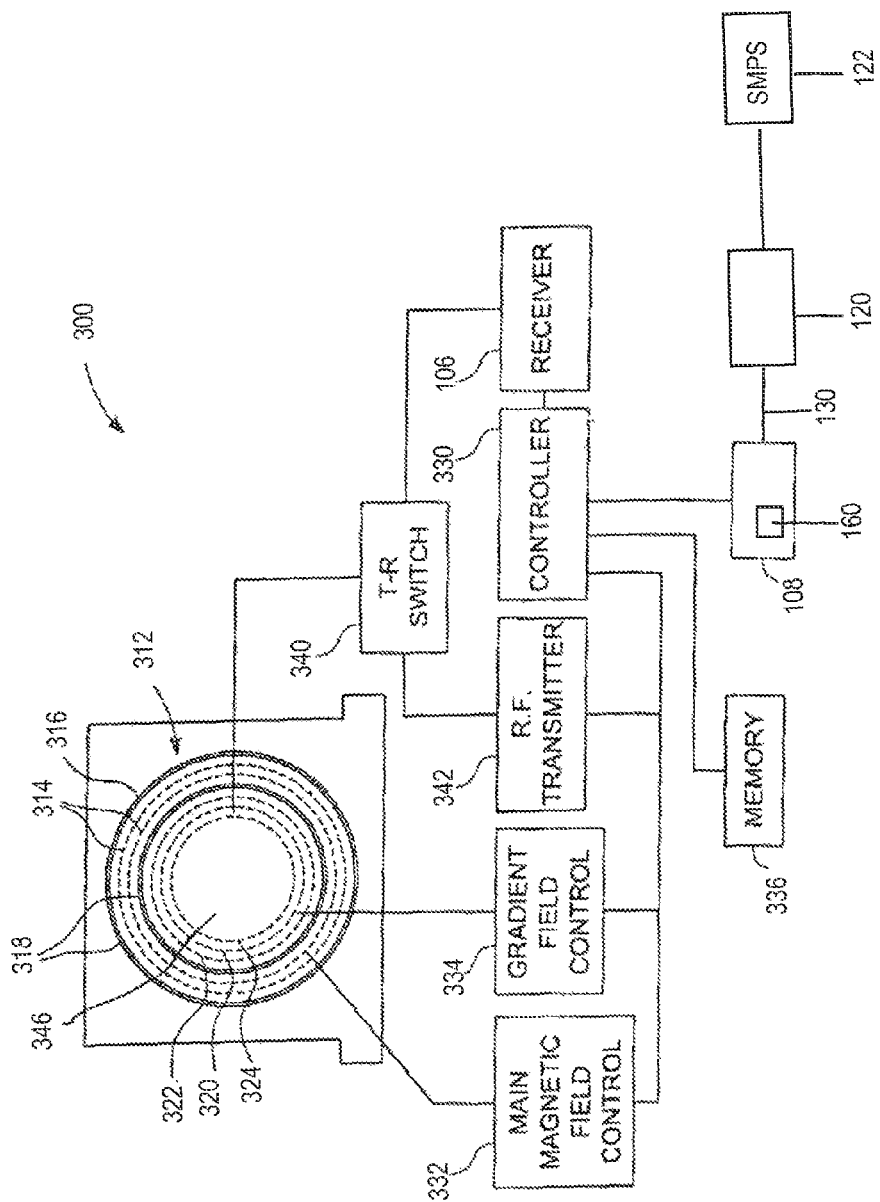
FIG. 4 is a block diagram of a magnetic resonance imaging (MRI) system formed in accordance with various embodiments.

Various embodiments of the NACS 100 and methods described herein may be provided as part of, or used with, a medical imaging system, such as an imaging system 300 as shown in FIG. 4. It should be appreciated that although the imaging system 300 is illustrated as a single modality imaging system, the various embodiments may be implemented in or with multi-modality imaging systems. For example, the imaging system 300 is illustrated as an MRI system which may be embodied as the MRI system 102 shown in FIG. 4 and may be combined with different types of medical imaging systems, such as a Computed Tomography (CT), Positron Emission Tomography (PET), a Single Photon Emission Computed Tomography (SPECT), as well as an ultrasound system, or any other system capable of generating images, particularly of a human. Moreover, the various embodiments are not limited to medical imaging systems for imaging human subjects, but may include veterinary or non-medical systems for imaging non-human objects, luggage, etc.

In the exemplary embodiment, the imaging system 300 includes a superconducting magnet assembly 312 that includes a superconducting magnet 314. The superconducting magnet 314 is formed from a plurality of magnetic coils supported on a magnet coil support or coil former. In one embodiment, the superconducting magnet assembly 312 may also include a thermal shield 316. A vessel 318 (also referred to as a cryostat) surrounds the superconducting magnet 314, and the thermal shield 316 surrounds the vessel 318. The vessel 318 is typically filled with liquid helium to cool the coils of the superconducting magnet 314. A thermal insulation (not shown) may be provided surrounding the outer surface of the vessel 318. The imaging system 300 also includes a main gradient coil 320, a shield gradient coil 322, and an RF transmit coil 324. The RF transmit coil 324 may be, for example, the RF coil 104 described above. The imaging system 300 also generally includes a controller 330, a main magnetic field control 332, a gradient field control 334, a memory 336, a display device 338, a transmit-receive (T-R) switch 340, an RF transmitter 342 and a receiver 344.

In operation, a body of an object, such as a patient (not shown), or a phantom to be imaged, is placed in the bore 346 on a suitable support, for example, a motorized table (not shown) or other patient table. The superconducting magnet 314 produces a uniform and static main magnetic field $B_1$ across the bore 346. The strength of the electromagnetic field in the bore 346 and correspondingly in the patient, is controlled by the controller 330 via the main magnetic field control 332, which also controls a supply of energizing current to the superconducting magnet 314.

The main gradient coil 320, which may include one or more gradient coil elements, is provided so that a magnetic gradient can be imposed on the magnetic field $B_1$ in the bore 346 in any one or more of three orthogonal directions x, y, and z. The main gradient coil 320 is energized by the gradient field control 334 and is also controlled by the controller 330.

The RF transmit coil 324 is arranged to transmit magnetic pulses and/or optionally simultaneously detect MR signals from the patient, if receive coil elements are not provided. The RF transmit coil 324 and a receive surface coil, or receive coil array, if provided, may be selectably interconnected to one of the RF transmitter 342 or receiver 344, respectively, by the T-R switch 340. The RF transmitter 342 and T-R switch 340 are controlled by the controller 330 such that RF field pulses or signals are generated by the RF transmitter 342 and selectively applied to the patient for excitation of magnetic resonance in the patient.

Following application of the RF pulses, the T-R switch 340 is again actuated to decouple the RF transmit coil 324 from the RF transmitter 342. The detected MR signals are in turn communicated to the controller 330 and the workstation 108. The workstation 108, including the noise analysis module 160, may be utilized to implement the methods described herein. More specifically, the workstation 108 may be configured to control the operation of the NACS 100 to vary the switching frequency of the SMPS 122. The controller 330 includes a processor 348 that controls the processing of the MR signals to produce signals representative of an image of the patient. The processed signals representative of the image are also transmitted to the display device 338 to provide a visual display of the image. Specifically, the MR signals fill or form a k-space that is Fourier transformed to obtain a viewable image which may be viewed on the display device 338.

In various embodiments, the RF coil 324 is configured to generate signals at one or more resonant frequencies, for example, centered about the Larmor frequencies of proton (hydrogen nuclei) and/or carbon (e.g., $^{13}C$ nuclei). However, it should be noted that the RF transmitter 342 may be configured to generate other frequencies causing different nuclei to resonate at their Larmor frequencies. Moreover, the MR signals and the image(s) generated may be encoded using any known technique in the art.

The various embodiments and/or components, for example, the modules, or components and controllers therein, such as of the imaging system 300, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As described above, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A noise abatement system comprising:
    a processor configured to measure noise in an imaging system and generate a switch mode power supply (SMPS) input signal based on the measured noise; and
    an adjustable switched mode power supply configured to receive the SMPS input signal and adjust a switching frequency of the switched mode power supply, based on the SMPS signal, to operate at a frequency that generates harmonics that are outside of an imaging bandwidth of the imaging system.

2. The noise abatement system of claim 1, wherein the imaging system is a Magnetic Resonance Imaging (MRI) system and the processor is further configured to:
    receive radio frequency (RF) information from an RF coil;
    measure the noise in the RF information; and
    generate the SMPS input signal based on the measured noise in the RF information.

3. The noise abatement system of claim 1, further comprising a frequency drive control device configured to receive an input signal from the processor and modify the input signal to generate the SMPS input signal.

4. The noise abatement system of claim 1, wherein the SMPS comprises a voltage controlled oscillator.

5. The noise abatement system of claim 1, wherein the processor is further configured to measure noise in a magnetic resonance imaging system and generate the SMPS input signal based on the measured noise.

6. The noise abatement system of claim 1, further comprising a noise analysis module configured to measure coherent noise in a Magnetic Resonance Imaging (MRI) system and generate the SMPS input signal based on the measured noise.

7. The noise abatement system of claim 1, wherein the imaging system is a Magnetic Resonance Imaging (MRI) system, and the noise abatement system further comprises a noise analysis module configured to:
    receive a RF signal from an RF coil, the RF coil measuring noise while the SMPS is activated;
    measure coherent noise in the received RF signal using a coherent noise test; and
    vary a switching frequency of the SMPS based on the measured coherent noise.

8. The noise abatement system of claim 1, further comprising an Ethernet connection between the processor and the SMPS.

9. A magnetic resonance imaging (MRI) system comprising:
    an RF coil; and
    a noise abatement system coupled to the RF coil, the noise abatement system comprising
    a processor configured to receive RF information from the RF coil, measure noise in the MRI system using the RF information, and generate a switch mode power supply (SMPS) input signal based on the measured noise; and
    an adjustable switched mode power supply configured to receive the SMPS input signal and adjust a switching frequency of the switched mode power supply, based on the SMPS signal to operate at a frequency that generates harmonics that are outside of an imaging bandwidth of the MRI system.

10. The MRI system of claim 9, further comprising a frequency drive control device configured to receive an input signal from the processor and modify the received input signal to generate the SMPS input signal.

11. The MRI system of claim 9, wherein the SMPS comprises a voltage controlled oscillator.

12. The MRI system of claim 9, further comprising a noise analysis module configured to measure coherent noise in the MRI system and generate the SMPS input signal based on the measured coherent noise.

13. The MRI system of claim 9, further comprising a noise analysis module configured to:
    receive the RF signal from an RF coil, the RF coil measuring noise while the SMPS is activated;
    measure coherent noise in the received RF signal using a coherent noise test; and
    vary a switching frequency of the SMPS based on the measured coherent noise.

14. The MRI system of claim 9, further comprising an Ethernet connection between the processor and the SMPS.

15. A method for calibrating a magnetic resonance imaging (MRI) system, said method comprising:
    measuring noise in the MRI imaging system;
    generating a signal based on the measured noise; and
    adjusting a switching frequency of a switched mode power supply (SMPS) based on the signal to operate at the system at a frequency that generates harmonics that are outside of an imaging bandwidth of the MRI imaging system.

16. The method of claim 15, further comprising:
    deactivating the SMPS, and
    determining a baseline noise level with the SMPS deactivated.

17. The method of claim 16, further comprising:
    activating the SMPS; and
    generating the signal with the SMPS activated.

18. The method of claim 15, further comprising:
    operating the SMPS at a nominal switching frequency; and
    determining a noise level while the SMPS is operating at the nominal frequency.

19. The method of claim 15, further comprising:
    iteratively measuring the in the imaging system while the SMPS is activated; and
    iteratively adjusting the switching frequency of the SMPS until the SMPS operates at a frequency that generates harmonics that are outside of the imaging bandwidth of the imaging system.

20. The method of claim 15, wherein measuring the noise further comprises measuring coherent noise in the received RF signal using a coherent noise test.

* * * * *